Figure 1:
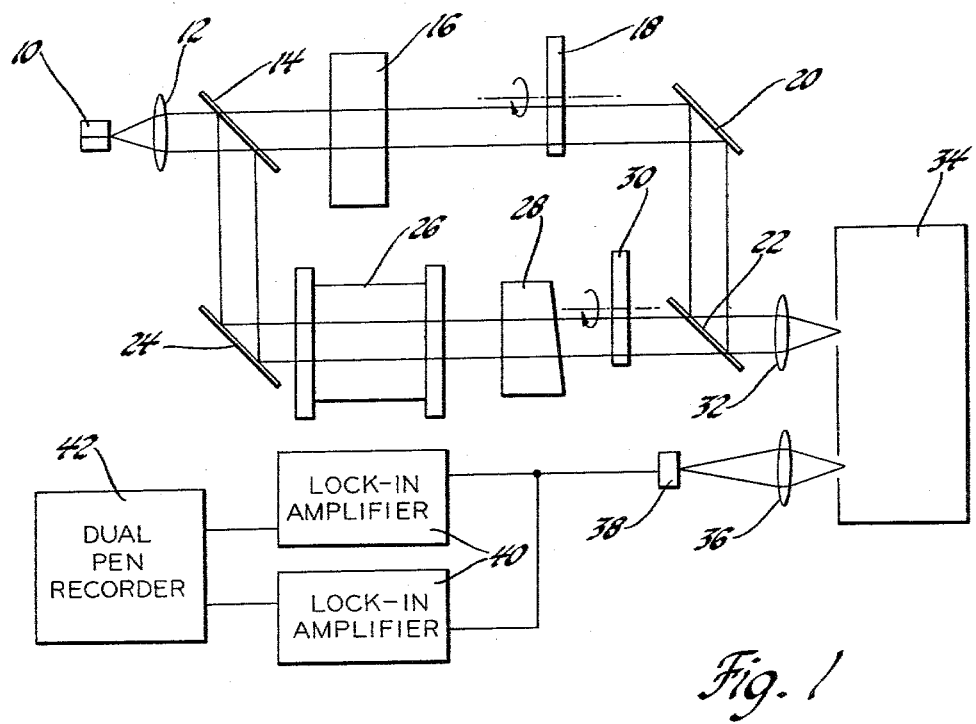

United States Patent [19]

Chraplyvy

[11] 4,241,997
[45] Dec. 30, 1980

[54] LASER SPECTROMETER WITH FREQUENCY CALIBRATION

[75] Inventor: Andrew R. Chraplyvy, Troy, Mich.

[73] Assignee: General Motors Corporation, Detroit, Mich.

[21] Appl. No.: 968,352

[22] Filed: Dec. 11, 1978

[51] Int. Cl.³ .............................................. G01J 3/34
[52] U.S. Cl. .................................. 356/309; 356/323; 356/326; 356/243
[58] Field of Search ............... 356/308, 309, 319, 320, 356/321, 323, 324, 325, 326, 328

[56] References Cited

U.S. PATENT DOCUMENTS 3,521,959  7/1970  Treharne .............................. 356/309

OTHER PUBLICATIONS

"Wavenumber Calibration of Tunable Diode Lasers Using Etalons", Flicker et al, Applied Optics, vol. 17, No. 6, Mar. 15, 1978, pp. 851–852.

Primary Examiner—Vincent P. McGraw
Attorney, Agent, or Firm—Warren D. Hill

[57] ABSTRACT

A laser beam from a tunable laser is split into two paths containing an etalon and a sample cell respectively. The two paths are chopped at different frequencies. The paths are combined and fed to a monochromator and then detected by a single detector. Lock-in amplifiers tuned to the chopper frequencies and responsive to the detector output produce signals corresponding to the spectra arising from the etalon and the sample gas absorption. A recorder simultaneously displays the two spectra.

1 Claim, 2 Drawing Figures

U.S. Patent    Dec. 30, 1980    4,241,997

LASER SPECTROMETER WITH FREQUENCY CALIBRATION

This invention relates to a laser spectrometer including frequency calibration apparatus.

In a typical spectroscopic measurement involving tunable lead-salt diode lasers, a monochromator isolates single laser cavity modes and provides a rough frequency scale. However, a Fabry-Perot etalon is required to generate accurate frequency markers. Sample and etalon spectra can be recorded successively, using a single detector, or simultaneously, using a split-beam, two-detector arrangement. In the former arrangement current and temperature drifts between successive frequency scans introduce errors in frequency measurement. In the latter arrangement the laser beam is split after it passes through a monochromator. It has been shown that such an arrangement introduces frequency calibration errors when a single-pass monochromator is used. That phenomenon is discussed in the publication by Flicker et al Appl. Opt. 17, 851 (1978).

It is, therefore, an object of the invention to provide a laser spectrometer apparatus which is free of errors in frequency measurement induced by temperature drifts as well as yfrequency calibration errors.

The invention is carried out by providing a tunable laser and a beam splitter for forming two energy beam paths, one path including a Fabry-Perot etalon and a chopper operating at a first frequency and the other path containing a sample chamber and a chopper operating at a second frequency, means for combining the two paths and passing the energy through a monochromator to a detector, and lock-in amplifiers tuned to the first and second frequency, respectively, and responsive to the detector output for providing absorption spectra and frequency calibration signals which are simultaneously recorded by a recorder.

Figure 2:
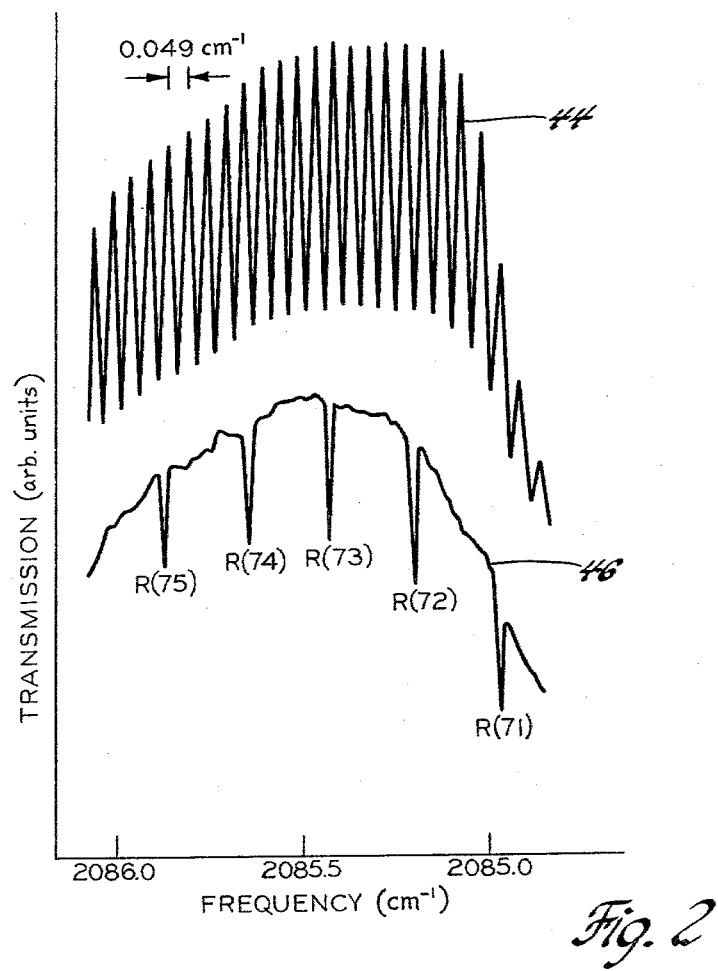

The above and other advantages will be made more apparent from the following specification taken in conjunction with the accompanying drawings wherein like reference numerals refer to like parts and wherein:

FIG. 1 is a schematic diagram of a laser spectrometer according to the subject invention, and FIG. 2 is an illustration of simultaneously recorded absorption and calibration spectra obtained by using the apparatus of FIG. 1.

The apparatus as shown in FIG. 1 includes a tunable lead-salt diode laser 10 which emits a beam that is collimated by a lens 12. A beam splitter 14 separates the beam into two paths. The first path contains a Fabry-Perot etalon 16 and a chopper 18 which interrupts the first path at a first frequency. A mirror 20 directs the beam in the first path to a second beam splitter 22 where the two beam paths are combined. The second beam path is directed by a mirror 24 through a sample chamber 26 containing the gas or other material being analyzed, a germanium wedge 28 and a second chopper 30 operating to interrupt the second beam at a second frequency. The beams after being recombined by the beam splitter 22 are passed through a lens 32, a monochromator 34 and a final lens 36 which focuses the beams onto a single detector 38. First and second lock-in amplifiers 40 tuned to the first and second frequencies, respectively, provide output signals representing the etalon and sample absorption spectra to a dual pen recorder 42 which simultaneously records the signals.

In operation the laser diode 10 operates simultaneously in a plurality of modes to thereby emit radiant energy at a plurality of widely spaced frequencies. The function of the monochromator 34 is to filter out all the frequencies except one occurring in a preselected band for application to the detector 38. According to the usual practice of spectrometry, the selected frequency of the laser beam is swept through a frequency range in order to determine the absorption of the sample material at each point in the frequency range. Thus, the second beam passing through the sample chamber 26 is modulated according to the absorption characteristics of the sample material. The germanium wedge 28 serves to equalize the path length of the two beams. The etalon 16 in the first beam path produces very accurately spaced interference peaks in the spectra. The lock-in amplifiers 40 are tuned to the first and second chopper frequencies, respectively, so that each amplifier detects and produces an output signal corresponding to the spectral signal of the first or second beam path, respectively. The lock-in amplifier multiplies the detector output signal and a reference signal representing a chopper frequency, and time averages the product. All the signal frequencies not the same as the reference frequency cancel out. The amplifier output signal contains only that detector signal which is synchronous with the reference signal.

The dual pen recorder simultaneously records two spectra as shown in FIG. 2, each corresponding to one of the beam paths. The upper trace 44 is the interference fringe pattern produced by the etalon 16 in the first beam path and provides a series of accurately and uniformly spaced peaks useful as a calibration standard. The lower trace 46 is the transmission spectra through a sample gas and contains absorption peaks characteristic of the particular gas being sampled.

In particular, the spectra of FIG. 2 was obtained by the apparatus of FIG. 1 comprising a $PbS_{0.82}Se_{0.18}$ laser operated at a temperature of about 17.5 K which generated the tunable radiation which was detected by a liquid nitrogen cooled HgCdTe detector manufactured by Texas Instruments. The lock-in amplifiers were Model HR 8 manufactured by Princeton Applied Research Corp., and the recorder was a dual pen recorder manufactured by Hewlett Packard. The lower trace is the transmission spectrum of 2.76 cm of carbonyl sulfide at $3 \times 10^3$ Pa. The upper trace shows the etalon fringes generated by a germanium etalon with a 0.049 $cm^{-1}$ free spectral range. The chopper frequencies were 470 Hz and 740 Hz, respectively, for the choppers 18 and 30. The monochromator was a Model E-1 double pass monochromator manufactured by Perkin-Elmer. The overall shape of the spectra is due to a convolution of the spectrometer slit function and the laser power spectrum. Measurements revealed that the "cross-talk" between the two signals was less than 0.1 percent of the total signal.

It will thus be seen that the laser spectrometer according to this invention is suitable for diode laser absorption measurements which records two spectra simultaneously using only one detector and eliminates frequency calibration errors previously encountered in one and two detector measurements.

The embodiments of the invention in which an exclusive property or privilege is claimed are defined as follows:

1. A laser spectrometer with frequency calibration comprising a tunable diode laser emitting a beam of radiant energy comprising a plurality of frequencies corresponding to a plurality of laser cavity modes, a beam splitter in the beam to produce first and second beam paths, an etalon in the first beam path for generating frequency markers for spectrometer calibration, a sample cell in the second beam path for containing a sample gas, means for chopping the first and second beam paths at first and second frequencies, respectively, a monochromator, means for combining the radiant energy from the two paths into a single beam and passing it through the monochromator to isolate the frequency corresponding to a single laser cavity mode, a single detector responsive to the single beam passed from the monochromator for generating an electrical signal analog of the single beam energy, lock-in amplifiers tuned to the first and second frequencies and responsive to the electrical signal for producing first and second simultaneous output signals corresponding to the radiant energy spectra arising from the etalon and the sample gas absorption, respectively, and recording means responsive to the two output signals for simultaneously displaying the sample absorption spectra and the etalon fringe spectra.

* * * * *